US009968733B2

(12) United States Patent
Haase et al.

(10) Patent No.: US 9,968,733 B2
(45) Date of Patent: May 15, 2018

(54) AIR TOLERANT IMPLANTABLE PISTON PUMP

(75) Inventors: James M. Haase, Maplewood, MN (US); Nicholas R. Whitehead, Hopkins, MN (US); Ronald L. Mezera, Lake Elmo, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1038 days.

(21) Appl. No.: 12/684,436

(22) Filed: Jan. 8, 2010

(65) Prior Publication Data

US 2010/0152714 A1    Jun. 17, 2010

Related U.S. Application Data

(63) Continuation-in-part of application No. 12/334,985, filed on Dec. 15, 2008, now abandoned.

(51) Int. Cl.
| | |
|---|---|
| *A61M 5/142* | (2006.01) |
| *F04B 17/04* | (2006.01) |
| *F04B 19/00* | (2006.01) |
| *F04B 35/04* | (2006.01) |
| *F04B 53/00* | (2006.01) |

(Continued)

(52) U.S. Cl.
CPC .... *A61M 5/14276* (2013.01); *A61M 5/14216* (2013.01); *F04B 17/042* (2013.01); *F04B 19/006* (2013.01); *F04B 35/045* (2013.01); *F04B 53/008* (2013.01); *F04B 53/1032* (2013.01); *A61M 5/165* (2013.01); *A61M 5/36* (2013.01); *A61M 2205/7518* (2013.01)

(58) Field of Classification Search
CPC .......... A61M 5/14216; A61M 5/14276; A61M 5/38; A61M 5/36; A61M 2205/7527; F04B 53/008; F04B 17/048

USPC ............ 604/151, 67, 288.01–288.04, 890.1, 604/891.1; 417/417
See application file for complete search history.

(56) References Cited

U.S. PATENT DOCUMENTS

| | | |
|---|---|---|
| 4,021,152 A | 5/1977 | Toyoda |
| 4,193,397 A | 3/1980 | Tucker |

(Continued)

OTHER PUBLICATIONS

PCT International Search Report as issued in International Application No. PCT/US02/28081, dated Jun. 18, 2003.
PCT Search Report and Written Opinion dated Feb. 25, 2011.

*Primary Examiner* — Bhisma Mehta
*Assistant Examiner* — Larry R Wilson
(74) *Attorney, Agent, or Firm* — Mucting, Raasch & Gebhardt, P.A.

(57) ABSTRACT

An implantable infusion device includes a reservoir for housing an infusion medium and a drive mechanism having an inlet chamber, a piston and a piston channel. The inlet chamber is in fluid communication with the reservoir. The piston channel is in fluid communication with the inlet chamber, and has a distal end and a proximal end, the proximal end being closer to the inlet channel than the distal end. The piston is axially moveable within the piston channel to drive infusion medium out of the distal end of the piston channel. The clearance between the piston and the channel is sufficiently small to prevent undissolved gas in the inlet chamber from passing through the clearance. The inlet chamber may be sufficiently large to allow undissolved gas to accumulate without adversely affecting the performance of the infusion device.

23 Claims, 5 Drawing Sheets

(51) Int. Cl.
  *F04B 53/10* (2006.01)
  *A61M 5/165* (2006.01)
  *A61M 5/36* (2006.01)

(56) References Cited

U.S. PATENT DOCUMENTS

| | | |
|---|---|---|
| 4,245,789 A | 1/1981 | Gray |
| 4,373,527 A | 2/1983 | Fischell |
| 4,391,620 A | 7/1983 | Geisel |
| 4,437,815 A | 3/1984 | McMullen |
| 4,468,221 A | 8/1984 | Mayfield |
| 4,557,726 A | 12/1985 | Reinicke |
| 4,568,250 A | 2/1986 | Falk |
| 4,569,641 A | 2/1986 | Falk |
| 4,573,994 A | 3/1986 | Fischell |
| 4,576,556 A | 3/1986 | Thompson |
| 4,594,058 A | 6/1986 | Fischell |
| 4,636,150 A * | 1/1987 | Falk .................. A61M 5/14216 310/104 |
| 4,684,368 A | 8/1987 | Kenyon |
| 4,692,147 A | 9/1987 | Duggan |
| 4,697,622 A | 10/1987 | Swift |
| 4,714,234 A | 12/1987 | Falk |
| 4,808,089 A | 2/1989 | Bucholtz |
| 4,883,467 A | 11/1989 | Franetzki |
| 4,931,050 A | 6/1990 | Idriss |
| 4,985,015 A | 1/1991 | Obermann |
| 5,066,282 A | 11/1991 | Wijay |
| 5,167,633 A | 12/1992 | Mann |
| 5,176,644 A | 1/1993 | Srisathapat |
| 5,318,521 A | 6/1994 | Slettenmark |
| 5,492,449 A | 2/1996 | Hunklinger |
| 5,514,103 A | 5/1996 | Srisathapat |
| 5,527,307 A | 6/1996 | Srisathapat |
| 5,797,733 A | 8/1998 | Falk |
| 5,975,437 A | 11/1999 | Streicher |
| 6,142,445 A | 11/2000 | Kawaguchi |
| 6,193,477 B1 | 2/2001 | Falk |
| 6,227,818 B1 | 5/2001 | Falk |
| 6,652,252 B2 | 11/2003 | Zabar |
| 6,740,059 B2 * | 5/2004 | Flaherty ............ A61M 5/14248 600/151 |
| 6,770,067 B2 | 8/2004 | Lorenzen |
| 6,805,093 B2 | 10/2004 | Zsoldos |
| 6,932,584 B2 | 8/2005 | Gray |
| 6,997,921 B2 | 2/2006 | Gray |
| 7,104,768 B2 | 9/2006 | Richter |
| 7,131,767 B2 | 11/2006 | Socci |
| 7,320,676 B2 | 1/2008 | Miesel |
| 2003/0050625 A1 * | 3/2003 | Lorenzen .......... A61M 5/14216 604/891.1 |
| 2004/0127852 A1 | 7/2004 | Gray |
| 2005/0075624 A1 | 4/2005 | Miesel |
| 2006/0276744 A1 * | 12/2006 | Falk .................... A61K 9/0019 604/67 |
| 2007/0219480 A1 * | 9/2007 | Kamen ................ G05D 7/0647 604/20 |
| 2007/0255227 A1 * | 11/2007 | Haase ............... A61M 5/14276 604/218 |
| 2007/0269332 A1 | 11/2007 | Miyahara et al. |
| 2007/0270782 A1 | 11/2007 | Miesel |
| 2008/0009837 A1 | 1/2008 | Miesel |
| 2008/0047836 A1 | 2/2008 | Stand |
| 2008/0063543 A1 | 3/2008 | Xu et al. |
| 2008/0243074 A1 | 10/2008 | Miesel |
| 2009/0048562 A1 | 2/2009 | Falk |
| 2009/0118711 A1 | 5/2009 | Haase |

* cited by examiner

AIR TOLERANT IMPLANTABLE PISTON PUMP

RELATED APPLICATION

This application is a Continuation-In-Part application of U.S. application Ser. No. 12/334,985, filed on Dec. 15, 2008, published as US 2009/0118711 on May 7, 2009, which application is incorporated herein by reference in its entirety to the extent that it does not conflict with the disclosure presented herein.

FIELD

The present disclosure relates generally to implantable infusion devices; in particular to implantable infusion devices employing piston drive mechanisms.

BACKGROUND

Treatment of diseases and ailments of the body often benefit from short- or long-term infusion of therapeutic compositions. While such therapeutic compositions may be administered extracorporeally, e.g., via transcutaneous injection, many patients benefit from the consistent and repeatable dosage provided by an implantable infusion device. Such devices may employ a reservoir for storing an infusible therapeutic composition and a pumping mechanism coupled to the reservoir for discharging the infusible fluid through an outlet of the device. The discharge outlet is typically connected to flexible medical tubing, e.g., a catheter, leading to a targeted delivery site within the patient. The infusion device may further include electronics to control delivery of the therapeutic composition to the patient in accordance with a prescribed schedule.

Implantable infusion devices are typically implanted subcutaneously, e.g., in the chest or abdominal cavity. The device reservoir may be accessible via a self-sealing, needle-penetrable septum. Such devices are typically implanted so that the septum is located generally directly beneath the skin. The septum provides a fluid passageway that permits the reservoir to be refilled periodically via a transcutaneous injection. Accordingly, the pump reservoir can be filled or refilled without requiring surgical removal from the patient's body, and further without requiring any other significant surgical procedure.

During initial filling or refilling of the reservoir, gas bubbles or gas dissolved or entrained in the infusible therapeutic composition may be introduced into the reservoir. Formation or introduction of gas bubbles in the reservoir can potentially lead to problems with the pumping mechanism that can result in inaccurate delivery of the therapeutic composition or pump failure. For many infusion devices, it is recommended to vent or aspirate the reservoir prior to refilling to remove air trapped in the reservoir. In some case, it is also recommended to degas the therapeutic composition prior to introducing the composition into the reservoir. Such processes can be time consuming and may not be fully effective, due in part to faulty technique.

While air bubbles can cause problems with many pumping mechanisms, with piston pumps air bubbles tend to cause inaccurate delivery of fluid due to the volume occupied by the air. Further many implantable infusion devices employing piston pumps include valves upstream or downstream of the piston. Air in the system may result in inoperability of the system due to inability to generate sufficient pressure to draw or force air through the valves or may require prolonged amounts of time to clear the air prior to resuming fully functional operation.

BRIEF SUMMARY

The present disclosure describes, among other things, implantable infusion devices employing piston pumps that can tolerate air bubbles. Such devices continue to function despite incomplete aspiration of the reservoir or degassing, if such procedures are warranted.

In various embodiments, an implantable infusion device includes a reservoir for housing an infusion medium and a drive mechanism having an inlet chamber, a piston and a piston channel. The inlet chamber is in fluid communication with the reservoir. The piston channel is in fluid communication with the inlet chamber, and has a distal end and a proximal end, the proximal end being closer to the inlet chamber than the distal end. The piston is axially moveable within the piston channel to drive infusion medium out of the distal end of the piston channel. The clearance between the piston and the channel is sufficiently small to prevent undissolved gas in the inlet chamber from passing through the clearance. For example, the clearance between the piston and the channel may be sufficiently small such that the infusion medium is retained in the clearance between the piston and the channel via capillary action and surface tension effects prevent the passage of undissolved gas through the clearance. The device may be configured to provide any suitably small clearance, such as a clearance between about 3 micrometers and about 10 micrometers.

The reservoir may be a positive pressure reservoir or a negative pressure reservoir, relative to ambient atmospheric pressure. For example, the reservoir, in some embodiments may be maintained at a pressure of, for example, greater than 5 psia, greater than 10 psia or between about 15 psia and 16 psia. Use of negative pressure reservoirs (e.g., abut 14 psia or less) presents special concerns, as the ability of a gas to dissolve in a solution, such as a fluid therapeutic composition, decreases as pressure decreases; thereby increasing the likelihood of air bubble formation within the reservoir and pumping mechanism. In such situations, it may be important to properly degas the therapeutic composition prior to delivering the composition to the reservoir. The ability to tolerate incomplete degassing would be desirable, as degassing procedures are time consuming and often suffer from improper technique.

Positive pressure reservoirs can also present special concerns. For example, proper functioning of a valves downstream of the piston channel are important in infusion devices employing positive pressure reservoirs. If the valve fails or is of too low of a cracking pressure, therapeutic fluid may be inadvertently pushed through the device and into the patient. However, due to concerns with air bubbles, the cracking pressure of such valves has been kept low to ensure that the drive mechanism can generate sufficient pressure to move the air bubble past the valve if such air bubbles are present and to maintain low energy consumption of the drive mechanism.

In various embodiments, regardless of whether the reservoir is a positive pressure or a negative pressure reservoir, the infusion devices described herein include a valve downstream, of the piston channel. The valve may have a cracking pressure that is between about 5 psi less than the reservoir pressure and about 5 psi more than the reservoir pressure. For example, the valve cracking pressure may be about the same as the reservoir pressure. If the reservoir pressure is between 15 and 19 psia, the valve cracking pressure may be 20 psia or greater to ensure that inadvertent or undesired administration of infusion medium is avoided. Similarly, infusion devices having negative pressure reservoirs (e.g. 14 psia or less) may also include a valve downstream of the piston channel to prevent undesired or inadvertent administration of a therapeutic fluid when subjected to lower atmospheric pressures, such as experienced at high elevations or on an airplane. With prior devices employing piston drive mechanisms, valves with high cracking pressures would not have been employed due to fear that if air were to pass through the channel, the drive mechanism could not compress the air sufficiently to overcome the cracking pressure, causing the pump to effectively fail. However, with devices as described herein where undissolved air cannot pass through the channel, the piston drive mechanism can readily infuse a fluid medium through the channel to overcome the cracking pressure, open the valve, and force fluid out of the device. Accordingly, the devices described herein can employ safety valves that might not have been possible or practicable with prior infusion devices employing piston drive mechanisms.

The infusion device may also include a filter disposed between the inlet chamber and the reservoir, wherein the filter is configured to prevent microorganisms from entering the inlet chamber from the reservoir. Such a filter will generally and beneficially prevent undissolved gas from passing from the reservoir into the inlet chamber. However, gas dissolved in the infusion medium may pass through the hydrophilic filter, and over time, some of the dissolved or entrained gas will be freed or come out of solution and will form air bubbles in the inlet chamber. Such bubbles cannot pass through the filter into the reservoir and cannot be removed by aspiration when the reservoir is replenished with infusion medium. Accordingly, over time an increased volume of the inlet chamber may be occupied with air bubbles. For at least this reason, prior devices employing piston drive mechanism-avoided placement of a filter between the reservoir and the inlet chamber. Yet, it has been found, as described herein, that when the piston to channel clearance is sufficiently small to prevent undissolved free gas bubbles from passing through the clearance, 70% or more of the inlet chamber volume can be occupied by undissolved gas. Accordingly, infusion devices as described herein can include the beneficial effects of preventing contaminated infusion medium from reaching the inlet chamber and thus being delivered to the patient.

One or more embodiments of the infusion devices described herein may provide one or more advantages relative to previously manufactured or described devices. For example and in addition to the advantages of including a microbial filter and a valve as described above, the devices described herein can tolerate a good deal of error associated with degassing and aspiration associated with a refill procedure, which can often be a source of concern for implantable devices employing a piston drive mechanism. These and other aspects and advantages will be apparent to one of skill in the art from the accompanying detailed description and drawings.

BRIEF DESCRIPTION OF THE DRAWINGS

Referring now to the drawings in which like reference numbers represent corresponding parts throughout.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope of spirit of the present invention. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, undissolved gas means gas not dissolved or entrained in an infusion medium. It will be understood that gas may transition from being dissolved or entrained in an infusion medium to being in a free undissolved state. When in a free and undissolved state and surrounded by infusion medium, the gas will tend to form bubbles. Gas and air are generally used herein interchangeably.

As used herein, "about" means +/−10% of the enumerated numerical value that it precedes. For example, "about" may mean +/−5%, or +/−3% of the enumerated numerical value that it precedes.

The present disclosure describes, among other things, implantable infusion devices employing piston pumps that can tolerate air bubbles. It has been found that piston pumps having a piston to bore clearance sufficiently small to prevent undissolved gas (i.e., gas not dissolved in infusion medium) from passing through a radial clearance channel formed between the piston and the bore. For example, it has been found that if the clearance is sufficiently small such that infusion medium flows through the clearance channel via capillary action, undissolved gas bubbles do not pass through the clearance channel. Further, it has been shown that placement of an antimicrobial filter, such as a 0.22 micron filter, between a reservoir and an inlet chamber for the piston drive mechanism can be tolerated. Previously, infusion devices employing piston pumps would not include such filters due to fear that they might trap air bubbles within the piston inlet chamber causing pump inaccuracy or malfunction. In addition, such a filter generally prevents removal of the air bubbles from of the inlet chamber via aspiration during refilling of the reservoir. However, as described herein, it has been discovered that a large amount of undissolved gas can be tolerated within the pump inlet chamber (e.g., 70% or more of the volume of the chamber) without any significant adverse consequences.

Prior to describing details regarding piston pump infusion devices configured to tolerate air bubbles, a general discussion of representative infusion devices and drive mechanisms is provided with regard to FIGS. 1, 2, 3A and 3B. Additional details regarding configurations for tolerating air bubbles are provided in the discussion related to FIGS. 4A, 4B, 5, 6A and 6B.

Figure 1:
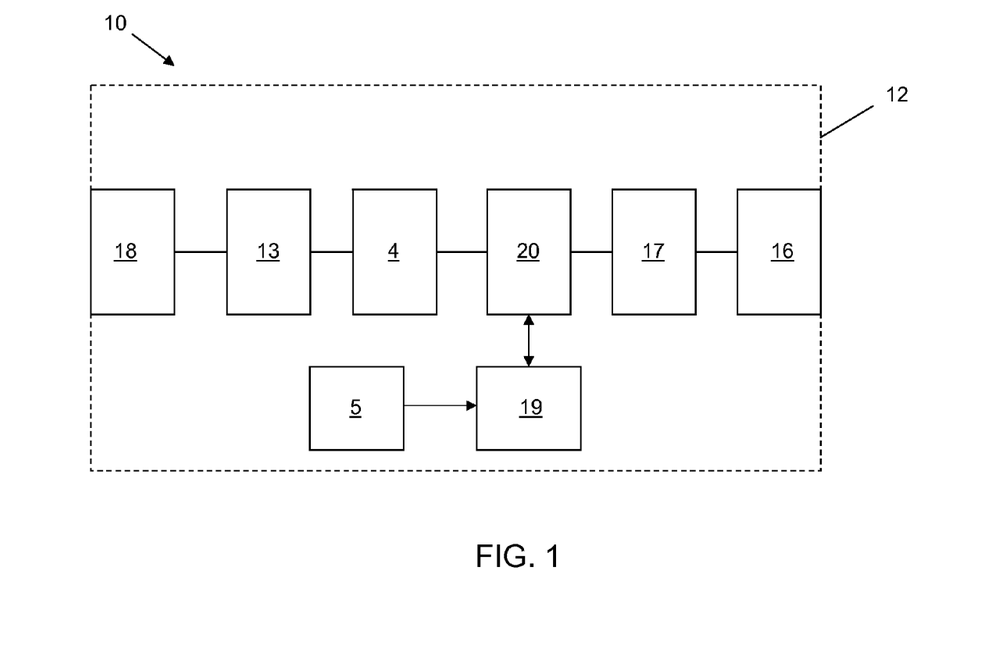
FIG. 1 is a block diagram illustrating some components of a representative infusion device.

Referring to FIG. 1, a block diagram of some components of a representative infusion device 10 is shown. The device includes a housing 12. Housing may be made of any suitable material, such as a rigid polymeric material or metallic material, such as titanium. If device 10 is configured to be implanted in a patient, the housing 12 is preferably hermetically sealed. In the depicted device 10, a fluid flow path includes an inlet 18, a reservoir 13, a filter 4, a drive mechanism 20, and an outlet 16. The flow path may also include a one-way valve 17 disposed between the drive mechanism 20 and the outlet 16, as depicted. The inlet 18 is fluidly coupled with reservoir 13, in which infusion medium may be stored. The inlet 18 may include a port through the housing 12 to allow access to the reservoir 18 or fluid path upstream of the reservoir. A septum may be disposed over the port to seal the inlet 18. The reservoir 13 is fluidly coupled to the drive mechanism 20, which may draw infusion medium from the reservoir 13. The filter 4 is configured to prevent microorganisms that may be in the infusion medium stored in the reservoir 13 from passing into the drive mechanism 20. The drive mechanism 20 is fluidly coupled to the outlet 16 and forces fluid drawn from the reservoir 12 out of the device 12 via the outlet 16. The outlet may include a port to which a catheter may be operably coupled. The infusion device 10 may include other components that are not shown in FIG. 1. For example, a one-way valve may be disposed between the inlet 18 and the reservoir 13 or between the reservoir 13 and the drive mechanism 20.

Representative examples of reservoirs 13 which may be employed in embodiments of infusion devices are described in U.S. Published Patent Application 2003/0050623, published Mar. 13, 2003, and entitled "Infusion Device and Reservoir for Same," which is incorporated herein by reference in its entirety to the extent that it does not conflict with the present disclosure. However, further embodiments may employ other suitable reservoir configurations, including, but not limited to, those described in U.S. Pat. No. 5,514,103 and U.S. Pat. No. 5,176,644, each to Srisathapat et al, U.S. Pat. No. 5,167,633 to Mann et al., U.S. Pat. No. 4,697,622 to Swift and U.S. Pat. No. 4,573,994 to Fischell et al.

In various embodiments, the reservoir 13 is a positive pressure reservoir, which means the pressure in the reservoir is greater than atmospheric pressure, forcing out the fluid contents of the reservoir 13 into the drive mechanism 20. A propulsion mechanism (not shown) may be operably coupled to the reservoir 13 to drive fluid out of the reservoir. Any suitable propulsion mechanism may be employed. By way of example, the reservoir 13 may be a bellows reservoir and the propulsion mechanism may contain a propellant chamber that contains a fluid whose vapor pressure is such that, under conditions of normal body temperature, pressure is exerted on the bellows to force liquid in the reservoir 13 to enter the drive mechanism 20. Examples of such propulsion mechanisms are found in Medtronic Inc.'s SYN-CHROMED and ISOMED implantable infusion devices. A mechanical spring may be readily substituted for the liquid propellant. Alternatively, the reservoir 13 may be formed, at least in part, of an elastomeric or resilient material biased in an empty configuration that expands when filled and forces fluid to exit reservoir 13 and enter the drive mechanism 20. Thus, the propulsion mechanism and reservoir may, in some embodiments, be the same component. A positive pressure reservoir 13 may be maintained at any suitable positive pressure by the propulsion mechanism or the elastic or resilient properties of the reservoir 13. Typically, ambient atmospheric pressure about 14.2 psia. In some embodiments, the positive pressure reservoir 13 is maintained at a pressure of greater than or equal to 15 psia, between 15 psia and 19 psia, between about 15 and about 16 psia, or between about 15.2 psia and about 15.5 psia.

In some embodiments, the reservoir 13 is a negative pressure reservoir, which means the pressure in the reservoir is greater than atmospheric pressure. For example, the reservoir 13 may be maintained at a pressure of less than or equal to 14 psia, less than or equal to 10 psia, or between 12 and 14 psia. In general, whether positive or negative pressure, the reservoir 13 may be maintained at a pressure of greater than 0 psia, greater than 5 psia, or greater than 10 psia, or greater than 15 psia.

Examples of inlet structures 18 that may be employed in embodiments of infusions devices 10 described herein are described in U.S. Pat. No. 7,186,236 to Gibson et al., entitled "Infusion Device And Inlet For Same;" U.S. Pat. No. 5,514,103 and U.S. Pat. No. 5,176,644, each to Srisathapat et al; U.S. Pat. No. 5,167,633 to Mann et al.; U.S. Pat. No. 4,697,622 to Swift; and U.S. Pat. No. 4,573,994 to Fischell et al.

Still referring to FIG. 1, the infusion device 10 includes electronics 19 and a power source 5 disposed in the housing 12. The electronics 19 are operably coupled to the power source 18 and are configured to control the drive mechanism 20. The power source 18 may include a battery, such as a rechargeable battery. Electronics 18 may include a processor for controlling the drive mechanism 20; memory for storing instructions, recording diagnostics, or the like; a telemetry module for wireless communication; a diagnostics module; or the like. Such modules and electronic components are well known to those of skill in the art and may be readily included and employed as desired.

Figure 2:
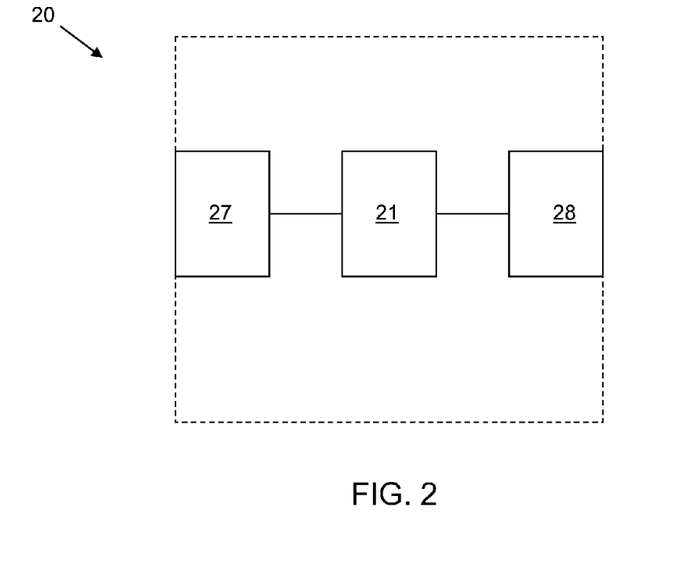
FIG. 2 is a block diagram illustrating some components of a representative drive mechanism.
Figure 3A:
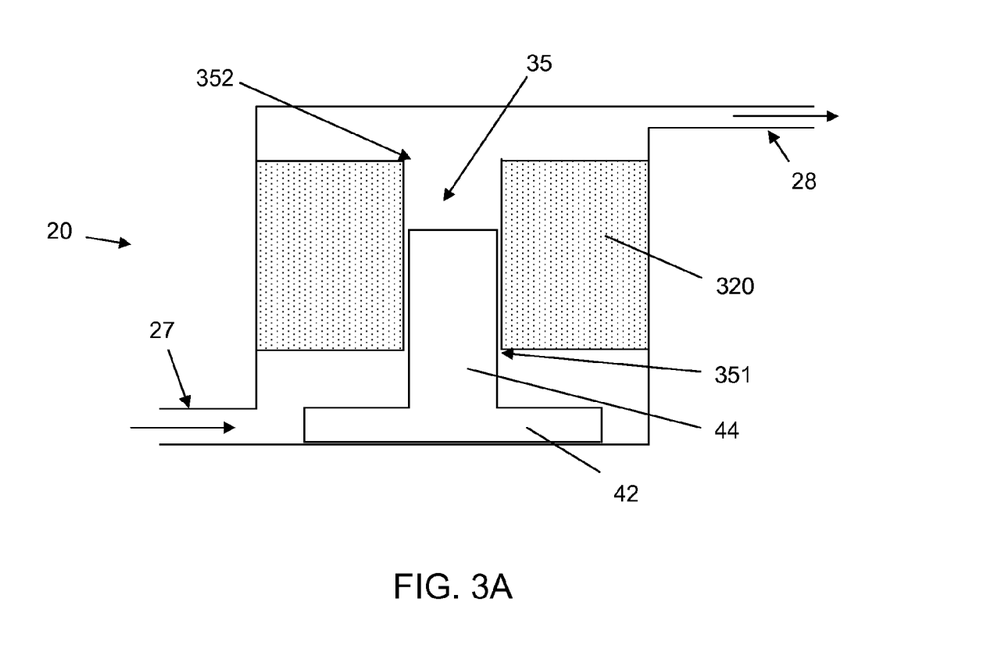
FIGS. 3A-B are schematic diagrams of cross sections illustrating some representative components of a drive mechanism.
Figure 3B:
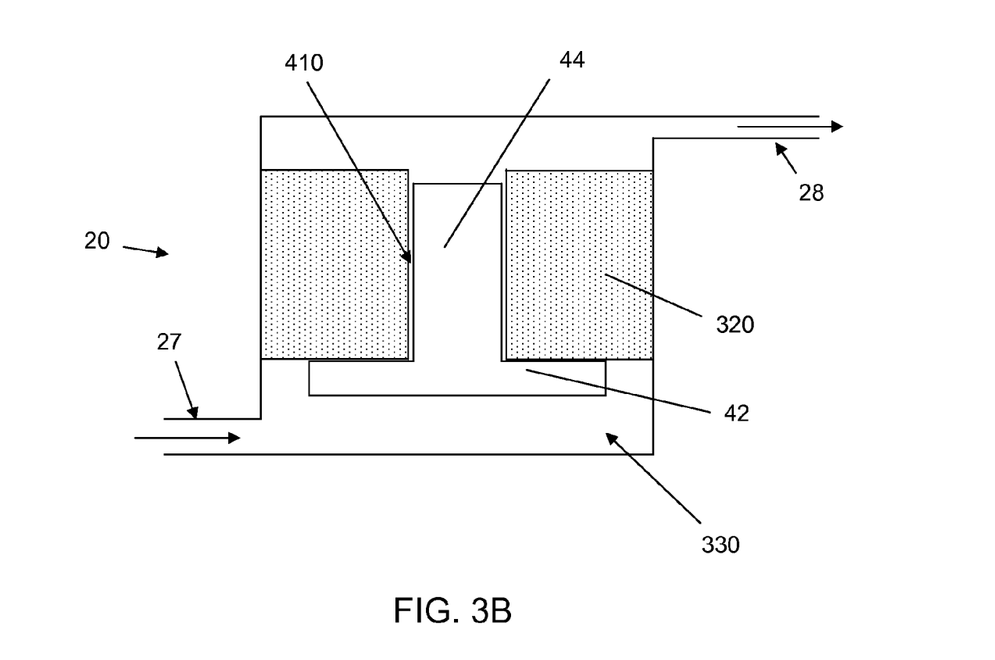

Referring now to FIGS. 2-3, representative components of piston drive mechanisms 20 are shown. In the block diagram of FIG. 2, the drive mechanism 20 includes an inlet 27, an outlet 28, and piston actuation mechanism 21. The piston actuation mechanism 21 is disposed in the flow path between the inlet 27 and the outlet 28. Some representative components of a piston drive mechanism 20 are shown in the schematic cross sectional views depicted in FIGS. 3A-B.

The drive mechanism 20 depicted in FIGS. 3A-B, includes and inlet 27, an outlet 28, a stationary portion 320 forming a channel 35, and an actuator having a piston 44 and an armature 42. In FIG. 3A, the piston 44 is in the retracted position. In FIG. 3B, the piston 44 is in the forward position. In various embodiments, the stationary portion 320 forming the channel 35 is integrally formed with a housing of the drive mechanism. The channel 35 has a proximal end 351, nearer the inlet 27, and a distal end 352, nearer the outlet 28. The piston 44 is positioned in, and axially movable within, the channel 35 to drive infusion medium out of the distal end 352 of the channel 35. A clearance 410 is formed between the piston 44 and the channel 35. Preferably, the clearance 410 is sufficiently small such that fluidic resistance between the piston 44 and the channel 35 causes a volume of infusion medium delivered during the forward portion of the pumping stroke to be greater than a volume of the infusion medium backflowing through the channel 35 during the retracting portion of the pumping stroke. As described in more detail below (e.g. with regard to FIGS. 5-6), the radial clearance 410 is sufficiently small to prevent sufficiently small to prevent undissolved gas in the inlet chamber 330 from passing through the radial clearance channel. The intended fluid flow path is indicated by arrows in FIGS. 3A-B. The armature 42 is operably coupled to the piston 44. In various embodiments, piston 44 is integrally formed with armature 42. The armature 42 and piston 44 together form an actuator.

As the piston 44 retracts (e.g., moves from the position shown in FIG. 3B to the position shown in FIG. 3A), infusion medium is drawn through inlet 27 to the piston channel 35. As the piston 35 is advanced, infusion medium is forced out of the channel 35 and out of the outlet 28. Electromagnetic energy causes the armature 42 to advance the piston 44 in the channel 35. A coil or solenoid may be disposed in the stationary member 320 forming the channel 35 to provide such electromagnetic energy. A mechanical biasing member (not shown), such as a spring, or electromagnetic force may allow the piston 44 to retract.

The drive mechanism 20 or components thereof, such as the armature 42, may be formed or configured in any suitable manner. In various embodiments, the drive mechanism or components thereof are drive mechanisms or components described in U.S. Patent Application Publication No. 2007/0168008, entitled "Implantable Therapeutic Substance Delivery Device Having a Piston Pump with and Anti-Cavitation Valve"; U.S. Patent Application Publication No. 2006/0206099, entitled "Low Profile Inlet Valve for a Piston Pump Therapeutic Substance Delivery Device"; U.S. Pat. No. 6,997,921, entitled "Infusion device and driving mechanism for same", or described in US Patent Application Publication No. 2009/0118711, published on May 7, 2009, entitled "Reduced-noise implantable infusion device", which patents and application are hereby incorporated herein by reference in their respective entireties to the extent that they do not conflict with the present disclosure.

Pistons and armatures as described herein may be made of any suitable material. For example, pistons or armatures may be formed from generally rigid, biocompatible and infusion medium compatible material, having a relatively high magnetic permeability such as, but not limited to, ferrous materials, ferritic stainless steel with high corrosion resistance, or the like. Pistons or armatures can also be fabricated with non-compatible materials and encased or plated in compatible materials. Pistons, armatures, or actuators may be molded, machined, or otherwise formed.

Figure 4A:
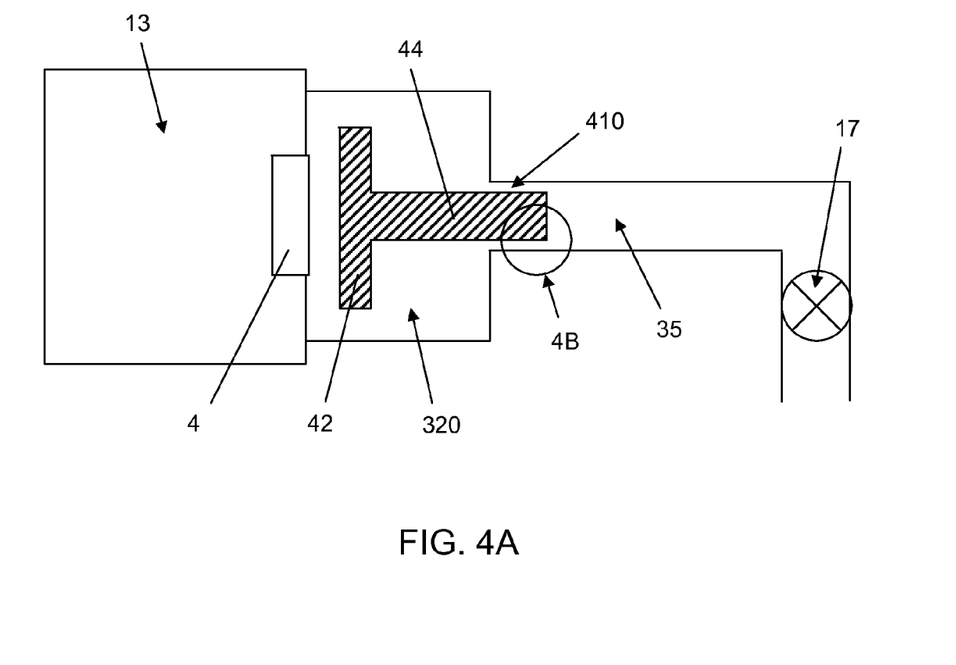
FIG. 4A is a schematic representative of selected components of an infusion device.
Figure 4B:
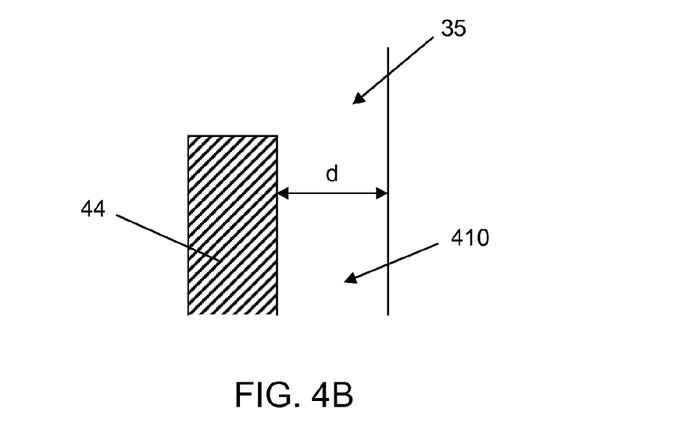
FIG. 4B is a schematic close-up view of the area within circle 4B of FIG. 4A.

Referring now to FIG. 4A, a schematic drawing of some components of a representative implantable infusion device are shown. The implantable infusion device includes an actuator having a piston 44 for pumping fluid from the inlet chamber 320 through a channel 35. A radial clearance 410 between the piston and channel is sufficiently small to prevent undissolved gas from passing from the inlet chamber 320 into the channel 35. Referring to FIG. 4B, which represents the area within the circle labeled 4B in FIG. 4A, the average distance d from a point on the exterior of the piston 44 to a closest point on the wall of the channel 35 in the clearance 410 is, in many embodiments, sufficiently small such that infusion media flows through the clearance 410 while undissolved air is prevented from passing through the clearance due to surface tension effects. The small clearance 410 provides fluidic resistance to prevent backflow and capillary retention of liquid to prevent passage of undissolved gas. While not intending to be bound by theory, it is believed that the liquid wets the surfaces of the clearance 410 and surface tension of the liquid prevents undissolved air from entering the channel 410. In some embodiments, the distance d between the piston 44 and the channel 35 is between 3 micrometers and 10 micrometers, such as about 6 micrometers. By having a sufficiently small clearance 410, where undissolved air or gas cannot escape between the piston 44 and the channel 35, by-pass valves may be eliminated which have been previously proposed for dealing with potential transmission of air. Such by-pass valves may be complex and may only be partially effective in eliminating problems associated with passing air through the channel, such as inaccurate fluid delivery and pump malfunction.

Still with reference to FIG. 4A, the device may include a valve 17 in communication with and downstream of the channel 35. In various embodiments, the valve 17 has a cracking pressure that is within about +/−5 psi of the pressure of the reservoir 13. In some embodiments, the valve 17 has a cracking pressure that is greater than the pressure of the reservoir 13; e.g. 1, 2, 3, or 5 psi or more than the pressure of reservoir. Higher valve cracking pressures (whether within +/−5 psi or greater than the reservoir pressure) may result in improved overall safety of the infusion device by preventing inadvertent or undesired leakage of infusion medium from the device. For example, if the reservoir 13 is a positive pressure reservoir and the piston 44 is in the retracted position relative to the channel 35, the positive pressure of the reservoir 13 may force infusion medium through the channel 35 and out of the device outlet in the absence of the valve 17. With prior devices employing piston drive mechanisms, valves with such a high relative cracking pressure would not have been employed due to fear that if air were to pass through the channel, the drive mechanism could not pump enough fluid to compress the air and overcome the cracking pressure, causing the pump to effectively fail. However, with devices as described herein where undissolved air cannot pass through the channel 35, the piston drive mechanism can readily infuse a fluid medium through the channel to overcome the cracking pressure, open the valve 17, and force fluid out of the device. In various embodiments, the reservoir 13 is a positive pressure reservoir maintained at between about 15 and 16 psia and the valve 17 has a cracking pressure of greater than 15 psi.

In various embodiments, the valve 17 has a cracking pressure that is 2 psi or greater than the reservoir 13 pressure minus the outlet pressure (ambient atmospheric pressure), when the difference is a positive number (i.e., the reservoir pressure is greater than ambient atmospheric pressure). As a patient with an implanted infusion device changes altitude, the pressure differential across the valve 17 changes. While the reservoir pressure remains fairly constant, the ambient pressure changes with altitude. If the valve cracking pressure is not sufficiently high to account for changes in altitude over a workable range, fluid from the reservoir may undesirably leak out of the device. For example, if the reservoir pressure is 15 psia and the ambient pressure is 10 psia, the pressure differential across the valve would be 5 psia. Accordingly, therapeutic fluid from the reservoir would leak across a valve having a cracking pressure of 5 psi or less in such a situation. To prevent such undesirable leakage, the valve 17 may have, in various embodiments, a cracking pressure that is 2 psi or greater than the reservoir 13 pressure minus the outlet pressure over the range of use of the device. In some embodiments, the valve 17 has a cracking pressure that is 3 psi or greater or 5 psi or greater than the reservoir 13 pressure minus the outlet pressure (ambient pressure) to further prevent undesired leakage.

A table of atmospheric pressures at different altitudes is presented below:

| Altitude (relative to sea level) | Pressure (psia) |
| --- | --- |
| −1,500 feet | 15.5 |
| 0 feet | 14.7 |
| 8,000 feet* | 10.9 |
| 10,000 feet | 10.1 |
| 15,000 feet | 8.3 |

*Most airplanes in flight are pressurized to the equivalent of 8,000 feet

Thus, if a device is designed to safely operate at altitudes of 15,000 feet, the valve cracking pressure should be equal to or greater than: [2+(reservoir pressure)−8.3 psia], which equals: (reservoir pressure −6.3 psia), if the reservoir pressure is greater than 8.3 psia. In many situations, a valve 17 having a cracking pressure of +/−5 psi of the reservoir 13 pressure will have a cracking pressure that is 2 psi or greater than the reservoir 13 pressure minus the outlet pressure over the range of use of the device.

In embodiments, when the piston motion is stopped at the end of the forward stroke, the valve-facing end of the piston 44 is in close proximity to the valve 17, for example, spaced from the valve member by no more than about ten percent (10%) of the piston diameter.

Still referring to FIG. 4A, the device also includes a reservoir 13 in fluid communication with an inlet chamber 320 of a drive mechanism. A filter 4 is disposed in the flow path between the reservoir 13 and the inlet chamber 320. The filter 4 is configured to prevent microorganisms that may be present in the reservoir 13 from entering the inlet chamber 320. Any suitable filter 4 may be employed. For example, a 0.22 micron filter is suitable for preventing microbes from passing from reservoir 13 into infusion chamber 320. It may be desirable for the filter 4 to be hydrophilic to allow infusion medium to readily cross from the reservoir 13 into the infusion chamber 320 through the filter 4. Examples of hydrophilic materials that may be used to form suitable filters include nylon and polyvinylidene fluoride. A hydrophilic filter 4 will generally and beneficially prevent undissolved gas from passing from the reservoir 13 into the inlet chamber 320. However, gas dissolved in the infusion medium may pass through the hydrophilic filter 4. Over time, some of the dissolved or entrained gas will be freed or come out of solution and will form air bubbles in the inlet chamber 320. Such bubbles cannot pass through the filter 4 into the reservoir 13 and cannot be removed by aspiration when the reservoir 13 is replenished with infusion medium. Accordingly, over time an increased volume of the inlet chamber 320 may be occupied with air bubbles.

Accordingly, it may be desirable for the volume of the inlet chamber 320 to be sufficiently large to accommodate a significant volume of undissolved gas that may accumulate over the service life of the infusion device. It has been found that when the clearance distance d between the piston 44 and the channel 35 is sufficiently small to prevent undissolved air from passing through the clearance 410, 70% or more of the volume of the inlet chamber 320 can be occupied with undissolved gas and the pump continues to deliver accurate amounts of infusion medium. While not relevant to infusion accuracy, high volumes of undissolved gas in the inlet chamber 320 can result in increased noise resulting from contact of the armature 42 with the stationary portion of the drive mechanism surrounding the proximal end of the channel 35. Armature designs configured to reduce noise, such as those described in US 2009/118711 (published on May 7, 2009, entitled REDUCED-NOISE IMPLANTABLE INFUSION DEVICE, which application is hereby incorporated herein by reference to the extent that it does not conflict with the present disclosure), may be employed. It should be noted that, while a large inlet chamber 320 volume may be desirable from the standpoint of providing for increased volumes of undissolved gas over the service life of the infusion device (e.g., longer service life would tend to result in larger volume), a large inlet chamber 320 volume may be undesirable for keeping the overall volume of the device small and because, in infusion devices employing bellows or collapsible reservoirs, infusion medium cannot be readily removed from the chamber 320 when the reservoir 13 is refilled due to the presence of the filter 4. Thus, larger chamber volumes may lead to increased volumes of stale infusion medium that can reside in the chamber 320. Accordingly, the size of the inlet chamber 320 should be balanced between the desire to maximize the volume of undissolved gas that the chamber can accommodate, the desire to reduce overall size of the device, and the desire to minimize the volume of stale drug that may remain in the chamber. In various embodiments, the inlet chamber 320 has a volume of between about 100 microliters and about 300 microliters. Such a volume may be desirable in an infusion device having a reservoir volume of between about 20 milliliters to about 50 milliliters and a service life of about 8 to 10 years. For infusion devices having larger or smaller reservoir volumes or service lives, it may be desirable for the inlet chamber volume to be larger or smaller in light of the considerations discussed above.

Figure 5:
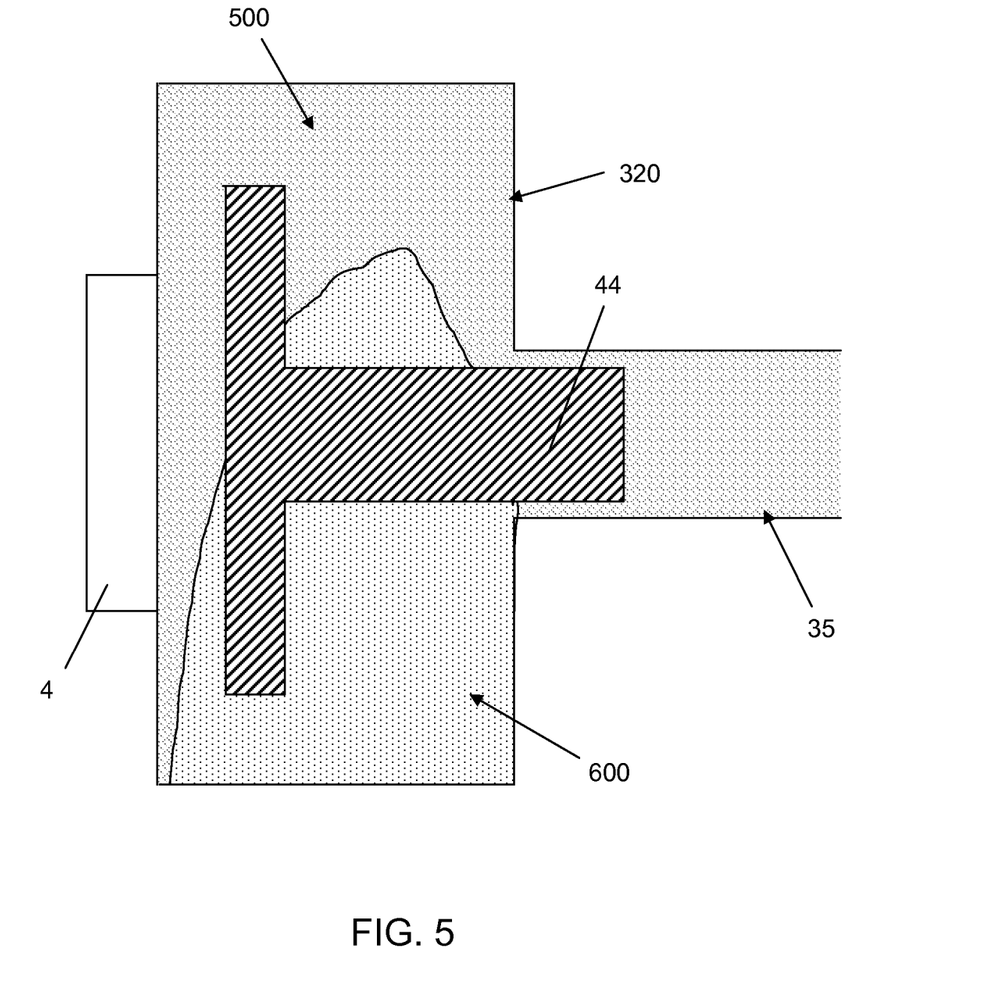
FIG. 5 is a schematic representative of selected components of an infusion device.
Figure 6A:
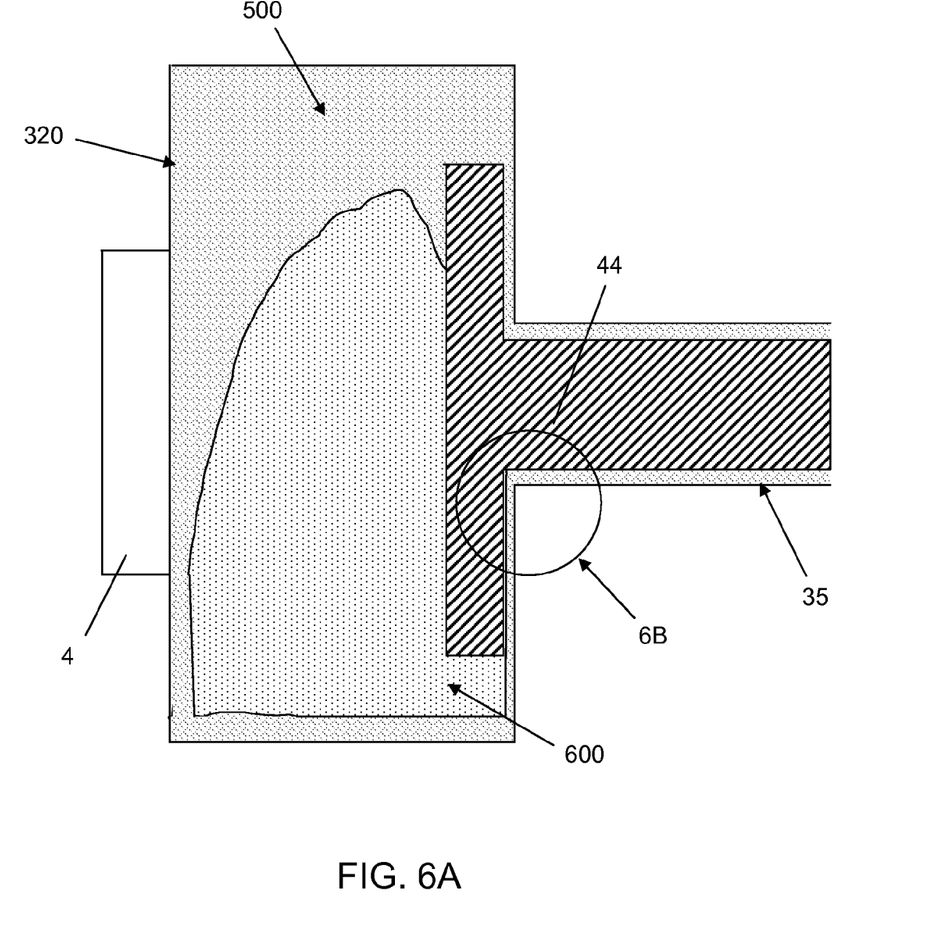
FIG. 6A is a schematic representative of selected components of an infusion device.
Figure 6B:
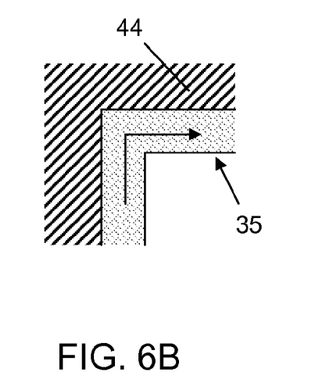
FIG. 6B is a schematic close-up view of the area within circle 6B of FIG. 6A.

Some of the concepts described above with regard to FIG. 4A are further discussed below with regard to FIGS. 5-6, in which selected portions or components of the device shown in FIG. 4A are shown. In FIGS. 5-6, a portion of the device including the filter 4, the inlet chamber 320, the piston 44 and the channel 35 is shown. Infusion medium 500 and an air bubble 600 are shown in the chamber 320. In FIG. 5, the piston 44 is in the retracted position and in FIG. 6A, the piston 44 is approaching the forward position. As the armature and piston 44 approach the forward position, the air bubble 600 is moved slightly away from the channel 35 and is displaced with infusion medium (see, e.g., FIG. 6B, which a close-up view of the area identified by circle 6B in FIG. 6A), allowing the infusion medium to enter the channel 35 while preventing the air bubble 600 or a portion thereof from entering the channel 35 due to the small clearance between the piston 44 and the channel 35. The liquid will wet the inlet chamber 320 and move freely around the gas bubbles or gas pocket. The undissolved gas will not enter the clearance due to wetting effects of the walls of the clearance channel 35 and surface tension of the liquid retained in the clearance via capillary action. As discussed above, the air bubble 600 or undissolved gas may occupy 70% or more of the volume of the inlet chamber 320 without adverse consequences of inaccurate fluid delivery when the clearance between the piston 44 and the channel 35 is sufficiently small to prevent the undissolved gas from entering the channel 35 from the inlet chamber 320.

Thus, embodiments of the AIR TOLERANT IMPLANTABLE PISTON PUMP are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable infusion device, comprising:
a reservoir for housing an infusion medium;
a drive mechanism having an inlet chamber, a piston and a piston channel,
wherein the inlet chamber is in fluid communication with the reservoir,
wherein the piston channel is in fluid communication with the inlet chamber, the piston channel having a distal end and a proximal end, the proximal end being closer to the inlet chamber than the distal end,
wherein the piston is axially moveable within the piston channel to drive infusion medium out of the distal end of the piston channel,
wherein the piston is positioned and moveable within the piston channel such that a clearance between the piston and the piston channel is sufficiently small to prevent undissolved gas in the inlet chamber from passing through the clearance;
a filter disposed between the inlet chamber and the reservoir, wherein the filter is hydrophilic and is configured to prevent microorganisms from entering the inlet chamber from the reservoir, wherein the filter is configured to allow dissolved gas to pass from the reservoir to the inlet chamber such that over time, the dissolved gas comes out of solution as undissolved gas in the inlet chamber, and wherein the filter is configured to prevent the undissolved gas from passing from the inlet chamber to the reservoir;
an outlet in fluid communication with the piston channel, the outlet being closer to the distal end of the piston channel than the proximal end of the piston channel; and
a valve in fluid communication with, and disposed between, the outlet and the piston channel,
wherein the piston has a valve facing end and a diameter, and wherein the valve facing end of the piston is spaced from the valve by a distance of about 10% of the piston diameter when the piston is in a forward position.

2. The implantable infusion device of claim 1, wherein the clearance between the piston and the piston channel is sufficiently small such that the infusion medium is retained in the piston channel via capillary action.

3. The implantable infusion device of claim 1, wherein the clearance between the piston and the piston channel is between 3 micrometers and 10 micrometers.

4. The implantable infusion device of claim 1, wherein the filter is configured to filter particles larger than 0.22 microns in diameter.

5. The implantable infusion device of claim 1, wherein a volume of the inlet chamber is between 100 microliters and 300 microliters.

6. The implantable infusion device of claim 1, wherein the reservoir is maintained at a pressure of greater than 5 psia.

7. The implantable infusion device of claim 1, wherein the reservoir is maintained at a pressure of greater than 10 psia.

8. The implantable infusion device of claim 1, wherein the reservoir is maintained at a pressure of between 15 psia and 16 psia.

9. The implantable infusion device of claim 1, wherein the valve has a cracking pressure that is between 5 psi less than a pressure of the reservoir and 5 psi more than the pressure of the reservoir.

10. The implantable infusion device of claim 1, wherein the valve has a cracking pressure that is at least 2 psi greater than a difference of a reservoir pressure minus an outlet pressure at a lowest ambient atmospheric pressure that the device is designed to be subjected.

11. The implantable infusion device of claim 1, wherein the valve has a cracking pressure that is equal to or greater than a reservoir pressure minus 6.3 psia.

12. The implantable infusion device of claim 1, wherein the drive mechanism is capable of continued operation without undissolved gas exiting the distal end of the piston channel when 70% of a volume of the inlet chamber is occupied by undissolved gas.

13. An implantable infusion device, comprising:
a reservoir for housing an infusion medium, the reservoir being maintained at a pressure of greater than 8 psia;
a drive mechanism having an inlet chamber, a piston and a piston channel,
wherein the inlet chamber is in fluid communication with the reservoir, the inlet chamber having a volume of between 100 microliters and 300 microliters,
wherein the piston channel is in fluid communication with the inlet chamber, the piston channel having a distal end and a proximal end, the proximal end being closer to the inlet chamber than the distal end,
wherein the piston is axially moveable within the piston channel to drive infusion medium out of the distal end of the piston channel,
wherein the piston is positioned and moveable within the piston channel such that an average clearance between the piston and the piston channel is between 3 micrometers and 10 micrometers;
a filter disposed between the inlet chamber and the reservoir, wherein the filter is hydrophilic and is configured to prevent microorganisms from entering the inlet chamber from the reservoir, wherein the filter is configured to allow dissolved gas to pass from the reservoir to the inlet chamber such that over time, the dissolved gas comes out of solution as undissolved gas in the inlet chamber, and wherein the filter is configured to prevent the undissolved gas from passing from the inlet chamber to the reservoir;
an outlet in fluid communication with the piston channel, the outlet being closer to the distal end of the piston channel than the proximal end of the piston channel; and
a valve in fluid communication with, and disposed between, the outlet and the piston channel,
wherein the piston has a valve facing end and a diameter, and wherein the valve facing end of the piston is spaced from the valve by a distance of about 10% of the piston diameter when the piston is in a forward position.

14. The implantable infusion device of claim 13, wherein the reservoir is maintained at a pressure of greater than 10 psia.

15. The implantable infusion device of claim 13, wherein the reservoir is maintained at a pressure of between 14 psia and 19 psia.

16. The implantable infusion device of claim 13, wherein the valve has a cracking pressure that is between 5 psi less than the pressure of the reservoir and 5 psi more than the pressure of the reservoir.

17. The implantable infusion device of claim 13, wherein the valve has a cracking pressure that is at least 2 psi greater than a difference of the reservoir pressure minus an outlet pressure at a lowest ambient atmospheric pressure that the device is designed to be subjected.

18. The implantable infusion device of claim 13, wherein the valve has a cracking pressure that is equal to or greater than the reservoir pressure minus 6.3 psia.

19. The implantable infusion device of claim 13, wherein the drive mechanism is capable of continued operation without undissolved gas exiting the distal end of the piston channel when 70% of the volume of the inlet chamber is occupied by undissolved gas.

20. An implantable infusion device, comprising:
a reservoir for housing an infusion medium wherein the reservoir being maintained at a pressure;
a drive mechanism having an inlet chamber, a piston and a piston channel,
wherein the inlet chamber is in fluid communication with the reservoir,
wherein the piston channel is in fluid communication with the inlet chamber, the piston channel having a distal end and a proximal end, the proximal end being closer to the inlet chamber than the distal end,
wherein the piston is axially moveable within the piston channel to drive infusion medium out of the distal end of the piston channel,
wherein the piston is positioned and moveable within the piston channel such that an average clearance between the piston and the piston channel is between 3 micrometers and 10 micrometers;
a filter disposed between the inlet chamber and the reservoir, wherein the filter is hydrophilic and is configured to prevent microorganisms from entering the inlet chamber from the reservoir wherein the filter is configured to allow dissolved gas to pass from the reservoir to the inlet chamber such that over time, the dissolved gas comes out of solution as undissolved gas in the inlet chamber, and wherein the filter is configured to prevent the undissolved gas from passing from the inlet chamber to the reservoir;
an outlet in fluid communication with the piston channel, the outlet being closer to the distal end of the piston channel than the proximal end of the piston channel; and
a valve in fluid communication with, and disposed between, the outlet and the piston channel, wherein the valve has a cracking pressure that is between 5 psi less than the pressure of the reservoir and 5 psi more than the pressure of the reservoir,
wherein the piston has a valve facing end and a diameter, and wherein the valve facing end of the piston is spaced from the valve by a distance of about 10% of the piston diameter when the piston is in a forward position.

21. The implantable infusion device of claim 20, wherein the pressure of the reservoir is maintained at greater than 0 psia.

22. The implantable infusion device of claim 20, wherein the inlet chamber has a volume of between 100 microliters and 300 microliters.

23. An implantable infusion device, comprising:
a reservoir for housing an infusion medium;
a drive mechanism having an inlet chamber, a piston and a piston channel,
wherein the inlet chamber is in fluid communication with the reservoir,
wherein the piston channel is in fluid communication with the inlet chamber, the piston channel having a distal end and a proximal end, the proximal end being closer to the inlet chamber than the distal end,
wherein the piston is axially moveable within the piston channel to drive infusion medium out of the distal end of the piston channel,
wherein the piston is positioned and moveable within the piston channel such that an average clearance between the piston and the piston channel is between 3 micrometers and 10 micrometers;
a filter disposed between the inlet chamber and the reservoir, wherein the filter is hydrophilic and is configured to prevent microorganisms from entering the inlet chamber from the reservoir wherein the filter is configured to allow dissolved gas to pass from the reservoir to the inlet chamber such that over time, the dissolved gas comes out of solution as undissolved gas in the inlet chamber, and wherein the filter is configured to prevent the undissolved gas from passing from the inlet chamber to the reservoir;
an outlet in fluid communication with the piston channel, the outlet being closer to the distal end of the piston channel than the proximal end of the piston channel; and
a valve in fluid communication with, and disposed between, the outlet and the piston channel, wherein the valve has a cracking pressure that is at least 2 psi greater than a difference of a reservoir pressure minus an outlet pressure at a lowest ambient atmospheric pressure that the device is designed to be subjected,
wherein the piston has a valve facing end and a diameter, and wherein the valve facing end of the piston is spaced from the valve by a distance of about 10% of the piston diameter when the piston is in a forward position.

* * * * *